(12) United States Patent
Li et al.

(10) Patent No.: US 9,040,030 B2
(45) Date of Patent: *May 26, 2015

(54) MASCARA COMPOSITIONS CONTAINING AN OIL-DISPERSIBLE MICRONIZED WAX AND A WATER-DISPERSIBLE WAX

(75) Inventors: Chunhua Li, Hillsborough, NJ (US); Hy Si Bui, Piscataway, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/988,630

(22) PCT Filed: Dec. 30, 2011

(86) PCT No.: PCT/US2011/068065
§ 371 (c)(1),
(2), (4) Date: May 21, 2013

(87) PCT Pub. No.: WO2012/092546
PCT Pub. Date: Jul. 5, 2012

(65) Prior Publication Data
US 2013/0236410 A1 Sep. 12, 2013

Related U.S. Application Data

(60) Provisional application No. 61/428,318, filed on Dec. 30, 2010.

(51) Int. Cl.
*A61K 8/06* (2006.01)
*A61K 8/92* (2006.01)
*A61Q 1/10* (2006.01)
*A61Q 1/00* (2006.01)
*A61K 8/81* (2006.01)
*A61K 8/02* (2006.01)

(52) U.S. Cl.
CPC ... *A61K 8/06* (2013.01); *A61K 8/92* (2013.01); *A61Q 1/10* (2013.01); *A61Q 1/00* (2013.01); *A61K 8/8111* (2013.01); *A61K 8/8152* (2013.01); *A61K 8/927* (2013.01); *A61K 8/0241* (2013.01); *A61K 2800/412* (2013.01); *A61K 2800/652* (2013.01)

(58) Field of Classification Search
None
See application file for complete search history.

(56) References Cited

U.S. PATENT DOCUMENTS

| | | | |
|---|---|---|---|
| 5,599,547 A * | 2/1997 | Bartholomey et al. | ....... 424/401 |
| 6,946,123 B2 | 9/2005 | De La Poterie et al. | |
| 7,887,788 B2 | 2/2011 | De La Poterie et al. | |
| 7,923,002 B2 | 4/2011 | De La Poterie et al. | |
| 2003/0086951 A9 | 5/2003 | Piot et al. | |
| 2003/0198609 A1* | 10/2003 | Bunger | ........................... 424/59 |
| 2004/0242579 A1* | 12/2004 | Wagner | ........................ 514/241 |
| 2005/0069508 A1 | 3/2005 | Pays et al. | |
| 2005/0169949 A1 | 8/2005 | De La Poterie et al. | |
| 2005/0229332 A1 | 10/2005 | Bodelin et al. | |
| 2006/0099231 A1 | 5/2006 | De La Poterie et al. | |
| 2006/0134038 A1 | 6/2006 | De La Poterie et al. | |
| 2006/0193801 A1 | 8/2006 | Blin et al. | |
| 2009/0148929 A1* | 6/2009 | Tarasi et al. | ................. 435/262.5 |
| 2009/0311296 A1* | 12/2009 | Tarasi et al. | ................... 424/401 |
| 2011/0250148 A1* | 10/2011 | Mateu et al. | .................... 424/43 |
| 2012/0171141 A1 | 7/2012 | Bui et al. | |
| 2012/0171142 A1 | 7/2012 | Bui et al. | |
| 2012/0171145 A1 | 7/2012 | Bui et al. | |
| 2013/0101542 A1 | 4/2013 | Bui et al. | |
| 2013/0130959 A1 | 5/2013 | Li et al. | |

OTHER PUBLICATIONS

International Search Report Issued Aug. 24, 2012 in PCT/US11/68065 Filed Dec. 30, 2011.
U.S. Appl. No. 13/884,518, filed May 9, 2013, Kanji, et al.
U.S. Appl. No. 13/884,153, filed May 8, 2013, Li, et al.
U.S. Appl. No. 13/884,122, filed May 8, 2013, Li, et al.
U.S. Appl. No. 13/696,159, filed Jan. 24, 2013, Tong, et al.

* cited by examiner

*Primary Examiner* — Ernst V Arnold
*Assistant Examiner* — Kyung Sook Chang
(74) *Attorney, Agent, or Firm* — Oblon, McClelland, Maier & Neustadt, L.L.P.

(57) ABSTRACT

The invention relates to a composition comprising at least one water-dispersible wax and at least one oil-dispersible micronized wax which, if desired, can be prepared at room temperature.

14 Claims, No Drawings

MASCARA COMPOSITIONS CONTAINING AN OIL-DISPERSIBLE MICRONIZED WAX AND A WATER-DISPERSIBLE WAX

CROSS REFERENCE TO RELATED APPLICATION

This application claims the benefit of priority under 35 U.S.C. §119(e) from U.S. Provisional Application Ser. No. 61/428,318, filed Dec. 30, 2010, the entire contents of which is hereby incorporated by reference.

FIELD OF THE INVENTION

The present invention relates to mascara compositions comprising at least one micronized wax and at least one water-soluble wax. The mascara compositions have beneficial cosmetic properties including comfort upon application and improved volumizing, curling and/or shine properties, and can be prepared at room temperature, if desired.

DISCUSSION OF THE BACKGROUND

Mascaras are generally prepared on the basis of two types of formulations: aqueous mascaras referred to as cream mascaras, in the form of a dispersion of waxes in water, and anhydrous or low-water-content mascaras, referred to as water-resistant mascaras (referred to as "waterproof"), in the form of dispersions of waxes in organic solvents.

Aqueous mascaras mainly contain a surfactant system, for example based on triethanolamine stearate, which makes it possible to obtain a stable dispersion of particles of wax agglomerated in an aqueous phase. This system plays an important part in the obtaining of such a dispersion, in particular at the interface in the interactions between particles of wax. However, such mascaras have the disadvantages of, among other things, being dry, having poor flexibility and/or having poor consistency.

Further, mascara compositions are generally made with a significant amount of wax to provide eyelashes with volume upon application. In general, to be processed, such waxes need to be melted at a high temperature, requiring significant energy and cost inputs.

There is thus a need to develop a cosmetic composition, in particular for making up the eyelashes, making it possible to obtain a smooth and homogeneous deposit on the eyelashes, while exhibiting a consistency that is easy to work after application, which has improved volumizing, curling and/or shine properties. There is also a need for mascara compositions which can be prepared at low temperature to save energy and decrease costs.

SUMMARY OF THE INVENTION

The present invention relates to compositions for eyelashes and/or eyebrows comprising at least one micronized wax and at least one water-dispersible wax. Preferably, the composition is a mascara composition. Preferably, the composition is an emulsion.

The present invention also relates to methods of treating, caring for and/or making up eyelashes and/or eyebrows by applying compositions of the present invention to eyelashes and/or eyebrows in an amount sufficient to treat, care for and/or make up the eyelashes and/or eyebrows. Preferably, the composition is a mascara composition. Preferably, the composition is an emulsion.

The present invention also relates to methods of improving the volumizing, curling and/or shine properties of a composition for eyelashes and/or eyebrows, comprising adding to the composition at least one micronized wax and at least one water-dispersible wax. Preferably, the composition is a mascara composition. Preferably, the composition is an emulsion.

The present invention also relates to methods of making a composition for eyelashes and/or eyebrows comprising reacting at least one micronized wax and at least one water-dispersible wax to form the composition at or about room temperature. Preferably, the composition is a mascara composition. Preferably, the composition is an emulsion.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time.

The amount of composition remaining on the skin after the pre-ascertained amount of time may then be evaluated and compared. For example, a composition may be waterproof if a majority of the product is left on the wearer, e.g., eyelashes. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

Micronized Wax

According to the present invention, compositions comprising at least one micronized wax are provided. The micronized wax of the present invention is non-liquid at room temperature (25° C.) and atmospheric pressure. According to preferred embodiments, the at least one micronized wax is spherical. Particles of the micronized wax of the present invention have a diameter on the order of 1,000 micrometers or less. According to preferred embodiments, the external diameter is in a range between about 0.20 and 1,000 micrometers, preferably between about 1 and 500 micrometers, preferably between about 3 and 200 micrometers, and preferably between about 5 and 50 micrometers, including all ranges and subranges therebetween.

According to preferred embodiments of the present invention, the at least one micronized wax is oil-dispersible. "Oil-dispersible" is understood to mean that the at least one micronized wax is dispersed in an oil or a mixture of oils such that at least 50% of the wax has been dispersed, preferably 60%, preferably 70%, preferably 80%, preferably 90%, preferably 95%, and preferably 100%, including all ranges and subranges therebetween.

According to preferred embodiments, the micronized wax is hollow. The wax of the present invention may contain, if desired, suitable chemical and/or biological agents.

Suitable micronized waxes of the present invention include those described in U.S. patent application publication no. 2009/0311296, the contents of which are hereby incorporated by reference in their entirety. Commercially available suitable waxes include Universal Remediation's Bioboom product.

According to preferred embodiments, the at least one micronized wax is present in the composition of the present invention in an amount ranging from about 5 to 65% by weight, more preferably from about 10 to about 60% by weight, more preferably from about 15 to about 50% by weight based on the total weight of the composition, including all ranges and subranges within these ranges.

According to preferred embodiments, if other wax(es) are present in the composition, the micronized wax constitutes the main wax of the composition (that is, the composition contains more micronized wax than all other waxes combined on a weight basis, containing, for example, 51%, 60%, 70%, 80%, 90%, 95% micronized wax as compared to all other waxes present on a weight basis). According to a preferred embodiment, the composition contains micronized wax of the present invention but no other waxes.

Water-Dispersible Wax

According to the present invention, compositions comprising at least one water-dispersible wax are provided. "Water-dispersible" is understood to mean that the at least one wax has sufficient hydrophilic moieties such that it is dispersed in water. Preferably, the wax has up to 50% hydrophilic moiety, preferably 10-50%, preferably 20-40%, and preferably 25-35%, including all ranges and subranges therebetween.

According to preferred embodiments, the water-dispersible wax comprises a hydrophilic moiety which is an acrylic acid moiety or salt thereof which provides water dispersibility. According to particularly preferred embodiments, the acrylic acid moiety is polyacrylate or a salt thereof such as ammonium, potassium or sodium polyacrylate.

Suitable water-dispersible waxes include, but are not limited to, the "cold process waxes" available from Jeen such as, for example, polyethylene sodium polyacrylate (Jeespeerse®CPW-2; melting point 45-60° C.), polyethylene sodium polyacrylate (Jeespeerse®CPW-3; melting point 45-70° C.), polyethylene sodium polyacrylate (Jeespeerse®CPW-5; melting point 50-85° C.), beeswax yellow sodium polyacrylate (Jeespeerse®CPW-B; melting point 50-60° C.), cocoa butter ppp, beeswax yellow, sodium polyacrylate (Jeespeerse®CPW-BC; melting point 35-50° C.), stearic acid, ceteareth-20, cetyl stearyl alcohol, sodium polyacrylate (Jeespeerse®CPW-EW1LP; melting point 39-50° C.), cetearyl alcohol, stearic acid, glyceryl stearate, PEG-100 stearate, sodium polyacrylate (Jeespeerse®CPW-GCS; melting point 40-50° C.), cetearyl alcohol, polysorbate 60, sodium polyacrylate (Jeespeerse®CPW-P; melting point 48-52° C.), and sunflower wax, sodium polyacrylate (Jeespeerse®CPW-S; melting point 65-80° C.).

According to preferred embodiments, the water-dispersible wax is present in the composition of the present invention in a combined amount ranging from about 0.5 to 20% by weight, more preferably from about 1 to about 15% by weight, more preferably from about 3 to about 10% by weight based on the total weight of the composition, including all ranges and subranges within these ranges.

Oil

According to the present invention, compositions comprising at least one oil are provided.

Suitable oils include volatile and/or non-volatile oils. Such oils can be any acceptable oil including but not limited to silicone oils and/or hydrocarbon oils.

According to certain embodiments, the oil carrier comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the oil carrier comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the oil carrier comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

In accordance with the present invention, volatile hydrocarbons such as isododecane are particularly preferred.

According to preferred embodiments, the oil(s) are is present in the composition of the present invention in a combined amount sufficient to disperse (as discussed above) the micronized wax. Typically, the amount of oil present in the compositions of the present invention ranges from about 5 to 70% by weight, more preferably from about 10 to about 60% by weight, more preferably from about 20 to about 50% by weight based on the total weight of the composition, including all ranges and subranges within these ranges.

Water

According to the present invention, compositions comprising water are provided. According to preferred embodiments, sufficient water is present to allow formation of an emulsion composition such as, for example, an oil-in-water emulsion or a water-in-oil emulsion. Typically, the amount of water present in the compositions of the present invention ranges from about 5 to 80% by weight, more preferably from about 10 to about 70% by weight, more preferably from about 20 to about 60% by weight based on the total weight of the composition, including all ranges and subranges within these ranges.

Compositions of the present invention can optionally further comprise any additive usually used in the field(s) under consideration. For example, dispersants such as poly(12-hydroxystearic acid), antioxidants, sunscreens, preserving agents, particularly phenoxyethanol, fragrances, fibers, fillers, neutralizing agents, cosmetic and dermatological active agents such as, for example, emollients, moisturizers, vitamins, essential fatty acids, surfactants, silicone elastomers, pasty compounds, viscosity increasing agents such as additional waxes (for example, soft or adhesive waxes) or liposoluble/lipodispersible polymers, film forming agents, colorants, and mixtures thereof can be added. A non-exhaustive listing of such ingredients can be found in U.S. patent application publication nos. 2004/0170586 and 2009/0142289, the entire contents of which are hereby incorporated by reference. Further examples of suitable additional components can be found in the other references which have been incorporated by reference in this application. Still further examples of such additional ingredients may be found in the *International Cosmetic Ingredient Dictionary and Handbook* (9$^{th}$ ed. 2002).

According to preferred embodiments of the present invention, the compositions can further comprise a desired agent. The desired agent can be, for example, any colorant (pigment, dye, etc.), any pharmaceutically or cosmetically active agent, or any film forming agent known in the art. For example, a cosmetic makeup composition comprising colorant can provide colorant and/or film forming agent to a substrate (eyelash) during use to provide the substrate with the desired film and/or color. Similarly, a pharmaceutical or cosmetic composition comprising a pharmaceutically active agent can provide such active agent to the patient or consumer upon use.

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine and barium.

A particularly preferred colorant is a carbon black dispersion given its ability to be processed at low temperatures.

Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheological agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/ methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block)

or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

Suitable fibers include, but are not limited to, fibers which enable improvement of the lengthening effect. "Fiber" should be understood to mean an object of length L and diameter D such that L is much greater than D, D being the diameter of the circle in which the cross-section of the fibre is inscribed. In particular, the L/D ratio (or form factor) is selected in the band ranging from 3.5 to 2500, in particular from 5 to 500, and more particularly from 5 to 150. The fibers utilisable in the composition of the invention can be fibers of synthetic or natural origin, mineral or organic. They can be short or long, unitary or structured, for example, braided, hollow or full. They can be of any shape and in particular of circular or polygonal cross-section (square, hexagonal or octagonal) depending on the specific application envisaged. In particular, their ends are blunted and/or polished to avoid injury. They can be rigid or non-rigid fibers. They can be of synthetic or natural origin, mineral or organic. They can be surface treated or not, coated or not, and colored or not.

In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

Another preferred embodiment of the present invention is a composition which contains so little TEA-stearate that the presence of TEA-stearate does not affect the cosmetic properties of the composition. Preferably, the compositions are substantially free of TEA-stearate (i.e., contain less than about 0.5% TEA-stearate), essentially free of TEA-stearate (i.e., contain less than about 0.25% TEA-stearate) or free of TEA-stearate (i.e., contain no TEA-stearate).

According to preferred embodiments of the present invention, the compositions described above can be prepared at low temperatures (approximately room temperature) by adding the components of the composition in a vessel and agitating the vessel to distribute the components. For example, the micronized wax can be added to an oil such as isododecane to disperse the wax in the oil, and the water-dispersible wax can be added to water to disperse the wax in water, and then the water and oil phases (each of which may contain other ingredients) can be mixed together to form a composition.

According to other preferred embodiments, methods of treating, caring for and/or enhancing the appearance of eyelashes and/or eyebrows by applying compositions of the present invention to the keratinous material in an amount sufficient to treat, care for and/or enhance the appearance of eyelashes and/or eyebrows are provided. In accordance with these preceding preferred embodiments, the compositions of the present invention are applied topically to the desired area in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag or tackiness), increased volume properties, increased curl properties and/or increased shine wear properties are provided.

According to other embodiments of the present invention, methods of improving the volumizing, curling and/or shine properties of a composition, comprising adding at least one micronized wax and at least one water-dispersible wax to the composition are provided.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

| Phase | RM | % |
|---|---|---|
| A | Micronized Beeswax | 20 |
| A | Isododecane | 20 |
| B | Water | 36 |
| B | Polyethylene - Sodium Polyacrylate | 4 |
| C | Carbon black | 15 |

-continued

| Phase | RM | % |
|---|---|---|
| D | dispersions phenoxyethanol | 5 |
| Total | | 100 |

Procedure
(1) Phase A was mixed at room temperature under low shear 50-100 RPM
(2) Phase B was mixed at room temperature under low shear 50-100 RPM
(3) Phases A and B were mixed together at room temperature until they become uniform at 100 RPM
(4) Carbon Black Dispersions were added to the mixture.
(5) Phenoxyethanol was then added to the mixture.

What is claimed is:

1. A composition comprising at least one water-dispersible wax comprising at least one acrylic acid moiety or a salt thereof, at least one oil-dispersible micronized wax that is a combination of micronized beeswax and a micronized soy wax, at least one oil and water, wherein the composition is in the form of a mascara.

2. The composition of claim 1, wherein the composition is an emulsion.

3. The composition of claim 1, further comprising at least one colorant.

4. The composition of claim 1, further comprising at least one surfactant.

5. The composition of claim 1, wherein the oil-dispersible micronized wax constitutes the main wax of the composition.

6. The composition of claim 5, wherein the oil-dispersible micronized wax constitutes at least 70% by weight of the total amount of wax in the composition.

7. The composition of claim 1, wherein the at least one micronized wax constitutes 5% to 65% by weight of the total weight of the composition.

8. The composition of claim 1, wherein the at least one water-dispersible wax constitutes 0.5 to 20% by weight of the total weight of the composition.

9. A method of making up eyelashes comprising applying the composition of claim 1 to eyelashes.

10. A method of curling eyelashes comprising applying the composition of claim 1 to eyelashes.

11. A method of making the mascara composition, claim 1 the method comprising adding the at least one micronized wax to at least one oil to form and oil phase comprising the micronized wax, adding the at least one water-dispersible wax comprising at least one acrylic acid moiety or salt thereof to water to form an aqueous phase comprising the water-dispersible wax, and mixing the two phases to form a composition.

12. The method of claim 11, wherein the composition is an emulsion.

13. The method of claim 11, wherein mixing occurs at room temperature.

14. The composition of claim 1, wherein the at least one acrylic acid moiety or salt thereof is polyacrylate or a salt thereof.

* * * * *